US007290669B1

(12) United States Patent
Hansen et al.

(10) Patent No.: US 7,290,669 B1
(45) Date of Patent: Nov. 6, 2007

(54) UPFLOW BIOREACTOR HAVING A SEPTUM AND AN AUGER AND DRIVE ASSEMBLY

(75) Inventors: Carl S. Hansen, Garland, UT (US); Conly L. Hansen, North Logan, UT (US)

(73) Assignee: Utah State University, North Logan, UT (US)

( * ) Notice: Subject to any disclaimer, the term of this patent is extended or adjusted under 35 U.S.C. 154(b) by 0 days.

(21) Appl. No.: 11/553,518

(22) Filed: Oct. 27, 2006

(51) Int. Cl.
C02F 3/28 (2006.01)
(52) U.S. Cl. ...................... 210/525; 210/629
(58) Field of Classification Search ............... 210/525, 210/629
See application file for complete search history.

(56) References Cited

U.S. PATENT DOCUMENTS

| 2,586,739 | A | 2/1952 | Summers ............... 277/362 |
| 2,647,733 | A | 8/1953 | Knowles et al. ......... 366/286 |
| 2,680,602 | A | 6/1954 | Nelson et al. .......... 366/343 |
| 3,622,009 | A | 11/1971 | Bordner et al. ......... 210/528 |
| 3,787,316 | A | 1/1974 | Brink et al. ............ 210/6 |
| 3,837,493 | A | 9/1974 | Lin et al. .............. 210/197 |
| 3,988,026 | A | 10/1976 | Kemp ................... 277/369 |
| 4,062,549 | A | 12/1977 | Kemp ................... 277/377 |
| 4,350,588 | A | 9/1982 | Tsubota et al. ......... 210/208 |
| 4,822,056 | A | 4/1989 | Bowers ................. 277/366 |
| 5,039,111 | A | 8/1991 | Kemp ................... 277/500 |
| 5,409,610 | A | 4/1995 | Clark .................. 210/603 |
| 5,866,002 | A | 2/1999 | Yates et al. ........... 210/601 |
| 6,193,409 | B1 | 2/2001 | Brunson et al. ......... 366/331 |
| 6,911,149 | B2 * | 6/2005 | Hansen et al. .......... 210/603 |
| 6,916,025 | B2 | 7/2005 | Brisson ................ 277/637 |
| 7,022,293 | B2 | 4/2006 | Hogan ................. 422/184.1 |
| 2002/0117443 | A1 | 8/2002 | Bailey et al. .......... 210/602 |

FOREIGN PATENT DOCUMENTS

| JP | 2002061752 | 2/2002 |
| JP | 2003071498 | 3/2003 |

* cited by examiner

Primary Examiner—Chester T. Barry
(74) Attorney, Agent, or Firm—Workman Nydegger

(57) ABSTRACT

An upflow bioreactor includes a vessel having an inlet and an outlet configured for upflow operation. A septum is positioned within the vessel and defines a lower chamber and an upper chamber. The septum includes an aperture that provides fluid communication between the upper chamber and lower chamber. The bioreactor also includes an auger positioned in the aperture of the septum. The vessel includes an opening in the top for receiving the auger. The auger extends from a drive housing, which is position over the opening and provides a seal around the opening. The drive housing is adjustable relative to the vessel. The position of the auger in the aperture can be adjusted by adjusting the drive housing relative to the vessel. The auger adjustment mechanism allows the auger to be accurately positioned within the aperture. The drive housing can also include a fluid to provide an additional seal around the shaft of the auger.

23 Claims, 7 Drawing Sheets

UPFLOW BIOREACTOR HAVING A SEPTUM AND AN AUGER AND DRIVE ASSEMBLY

GOVERNMENT INTERESTS

Work described herein has been supported, in part by a grant from the United States Department of Agriculture and United States Department of Energy, grant number 68-3A75-3-153. Therefore, the Government may have certain rights in this invention.

BACKGROUND OF THE INVENTION

1. The Field of the Invention

The present invention relates to upflow bioreactors for decomposing organic materials. More particularly, the present invention relates to an upflow bioreactor having an auger and drive assembly.

2. The Related Technology

A bioreactor is a device that uses bacteria to promote the decomposition or "digestion" of organic waste material into simple organics and gaseous biogas products. Biogas is typically a mixture of methane, carbon dioxide, hydrogen sulfide, and other volatile organic compounds. If produced in sufficient quantities, the methane gas can be used as a fuel.

Anaerobic digestion in open storage vessels has historically been utilized in waste water management, especially in livestock production, to reduce or convert complex organic matter to a smaller volume. This method has proven to be economical by reducing the volume of waste handled and by volatilizing some metabolites into the atmosphere. One disadvantage of open storage vessels includes the inability to keep the anaerobic digestion process in balance, resulting in the release of malodorous gases and inefficient, incomplete conversion of digested organic matter into biogas. In addition, the slow rate of digestion and the poor quality of methane gas yielded makes the economic recovery of methane gas generally unfeasible in open storage vessels.

Many attempts have been made to decompose organic waste using closed vessels. One type of closed vessel reactor that has shown high decomposition rates is the upflow anaerobic sludge blanket reactor. In the reactor, waste material is introduced into the bottom of the reactor and forced up through the vessel where it passes through a blanket of bacteria, which decomposes the organic material and produces biogas that can be collected and used as a fuel.

To achieve high decomposition rates in an upflow bioreactor, the bacterial culture should be well established. One important advantage of an upflow bioreactor is that it can be operated continuously. Thus, once the bacterial culture is established, the high rate of digestion can be maintained for an extended period of time (e.g. months or even years).

Recently an upflow reactor has been developed that induces formation of the bacterial culture on startup and maintains a thicker or more enriched bacterial culture during operation. These benefits are achieved by placing a septum near the top of the fluid level of the reactor. The septum causes suspended solids to settle out of the fluid nearing the top of the reactor. These solids settle back into the sludge blanket where digestion continues. The solids that are retained by the septum often include bacteria. By retaining these solids in the digester, the septum maintains a better bacterial culture and facilitates more complete digestion.

To allow the effluent to exit the digester, the septum has an aperture. Since an aperture in an upflow bioreactor can plug, an auger is placed in the aperture. The auger hangs from the top of the digester and slowly turns to keep the aperture clear of solids.

Upflow digesters that include a septum and an auger can be difficult to construct because of the need to accurately line up the auger within the aperture of the septum. In addition, the top of the digester needs to be sealed to form a chamber for collecting biogas.

BRIEF SUMMARY OF THE INVENTION

The present invention is directed to an upflow bioreactor for decomposing organic materials to produce biogas. The bioreactors include a septum for improved digestion and an auger that is placed in an aperture of the septum to reduce plugging. The auger is connected to the vessel through a drive assembly (e.g., a gearbox and/or motor). The auger and drive assembly includes an adjustment mechanism for aligning the auger within the aperture of the septum.

In an embodiment of the invention, the bioreactor includes a vessel having an inlet, an outlet, and a top opening. A septum is positioned within the vessel and defines a lower chamber and an upper chamber. The septum has an aperture that provides fluid communication between the lower chamber and the upper chamber.

The top opening of the vessel allows a portion of the auger to exit the vessel and/or allows a portion of a drive assembly to be positioned within the vessel. The auger and the drive assembly are operably coupled to form an auger and drive assembly that can rotate the auger in a desired direction.

The housing of the drive assembly is mounted over the top opening of the vessel and forms a gas seal around the top opening. The auger extends from the drive housing and through the aperture in the septum. The drive housing includes a mounting adjustment mechanism that allows the mounting of the drive housing to be adjusted relative to the vessel. An adjustment in the drive housing relative to the vessel translates into an adjustment of the position of the auger relative to the septum.

In one embodiment, the adjustment mechanism includes (i) a compressible member positioned between the drive housing and the vessel and (ii) a plurality of spaced apart fasteners that upon tightening cause compression of the compressible member. The fasteners can be selectively compressed to cause non-uniform compression of the compressible member. The non-uniform compression causes the drive housing to tilt relative to the vessel. The tilting of the drive housing causes lateral movement of the auger relative to the septum.

One advantage of using a compressible member is that the lateral movement of the auger is generated from a pivoting motion with the pivot near the drive housing. Since the septum is a substantial distance away from the drive housing, a small amount of pivoting near the drive housing causes a much larger lateral movement of the auger near the septum. Another advantage of using a compressible member between the drive housing and the vessel is that the compressible member can be used to provide a good gas seal around the top opening of the vessel.

In an alternative embodiment, the adjustment mechanism includes a plurality of bolts that are movable within a slot. The slot is over-sized such that there is a gap between the bolt and the slot when the bolt is positioned within the slot. The gap between the bolt and the slot provides the range of adjustability for the drive housing and thus the adjustability of the auger.

The bolts and slots can be in various configurations. For example, in one embodiment, the bolts are fixed to the vessel and the slots are incorporated into the drive housing. In an alternative embodiment, the bolts can be fixed to the drive housing and the slots can be incorporated into a bracket attached to the vessel.

The mounting adjustment mechanism of the invention allows an auger to be accurately positioned within an aperture of a septum without the need to precision engineer the bioreactor vessel, septum, aperture, and auger and drive assembly. In addition, the auger and drive assembly can provide a good seal, which allows biogas to be collected, while allowing the auger to be easily adjusted. The adjustment mechanism of the present invention also allows the auger and drive assembly to be a single unit that can be easily removed for maintenance.

In one aspect of the invention, the auger and drive assembly includes a fluid filled gearbox that is attached to the bioreactor vessel and forms a gas seal around a top opening in the vessel. The auger is operably connected to and suspended from the gearbox through a drive shaft. In this embodiment, a gearbox bearing and the fluid within the gearbox provide a seal around the driveshaft that drives the auger. The gearbox and the auger form a single assembly that can be attached and removed from the bioreactor vessel as a single piece. Using the gearbox as a seal around a driveshaft used to operate the auger advantageously simplifies the task of sealing the opening in the digester for the auger.

These and other advantages and features of the present invention will become more fully apparent from the following description and appended claims as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which.

DETAILED DESCRIPTION OF EXEMPLARY EMBODIMENTS

I. Introduction

The upflow bioreactors of the present invention advantageously provide rapid decomposition of organic wastes. The bioreactors of the present invention include a septum that facilitates the retention of solids within the bioreactor and an auger that prevents the bioreactor from plugging. The auger is part of an auger and drive assembly. In one embodiment, the auger and drive assembly includes an auger adjustment mechanism that allows the drive assembly to be adjusted with respect to the vessel which in turn results in a lateral adjustment of the auger with respect to the septum. The foregoing are an example of means for laterally adjusting the auger relative to the septum, more particularly the aperture through the septum. According to another aspect of the invention, the auger and drive assembly provide a gas seal around a top opening in the vessel of the bioreactor.

II. Upflow Bioreactors

Figure 1:
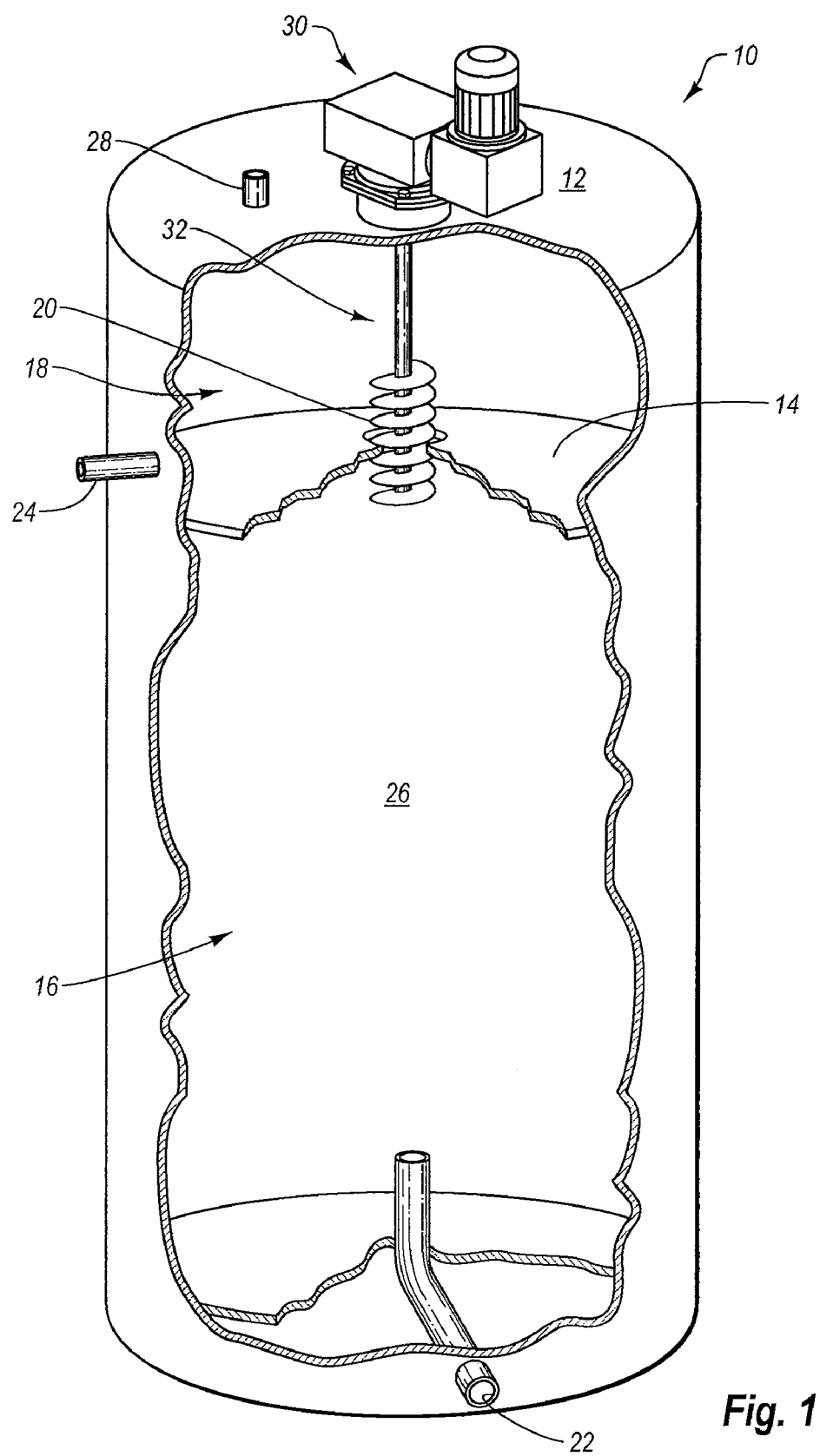
FIG. 1 illustrates an example of a bioreactor according to one embodiment of the present invention with a portion of the bioreactor removed to show the interior components.

FIG. 1 illustrates an exemplary bioreactor 10 according to one embodiment of the present invention. Bioreactor 10 includes a vessel 12 in which an organic material (e.g., sewage) can be introduced and held for treatment. A septum 14 is positioned in vessel 12 to form a lower chamber 16 and an upper chamber 18. An aperture 20 in septum 14 provides fluid communication between lower chamber 16 and upper chamber 18. Bioreactor 10 includes an auger 32 to facilitate the retention of solids suspended in the effluent passing through aperture 20 and to prevent the aperture 20 from becoming plugged. A drive assembly 30 generates and/or transfers a force for turning auger 32. Drive assembly 30 includes an adjustment mechanism (or means) for adjusting the position of auger 32 relative to aperture 20 in septum 14.

Bioreactor 10 is configured for upflow operation. An inlet 22 is provided in lower chamber 16 for introducing organic material to be decomposed. A pump is typically coupled to inlet 22 to provide pressure for introducing the organic material. An outlet 24 is placed in upper chamber 18 to allow effluent to exit bioreactor 10. The placement of inlet 22 in lower chamber 16 and the placement of outlet 24 in upper chamber 18 creates an upflow in bioreactor 10 during operation. The upflow in bioreactor 10 can be continuous or semi-continuous.

Lower chamber 16 includes a biomass 26. Biomass 26 includes a microbial culture and organic material to be decomposed. The upflow in bioreactor 10 is sufficiently slow that a sludge blanket of bacteria can form in the biomass 26 of lower chamber 16. The organic material (e.g., animal waste) is slowly forced up through the sludge blanket where it is decomposed into smaller organic molecules and biogas. The microbial culture present in biomass 26 is selected according to the particular organic material that is to be decomposed in bioreactor 10. In an exemplary embodiment, the microbial culture comprises anaerobic bacteria. Anaerobic bacteria can be naturally occurring in some organic wastes (e.g. non-sterile animal manure).

Any organic material can be decomposed in bioreactor 10 so long as a microbial culture is available for degrading the organic material and the organic material can be introduced into the bioreactor in a form that can be mixed with the microbes. Examples of suitable organic materials that can be digested in the bioreactors of the present invention include animal wastes produced from the farming, ranching, and agricultural industries, food processing waste, human waste, and the like.

In one embodiment, the type of microbial culture and type of organic material are selected such that the decomposition of the organic material produces biogas. Upper chamber 18 can be sealed such that biogas collects within upper chamber 18. A gas outlet 28 allows the biogas to be ported out of bioreactor 10. The biogas can advantageously be used as a fuel. For example, if desired, the biogas can be burned and the heat can be used to maintain an optimal operating temperature in bioreactor 10.

Figure 2:
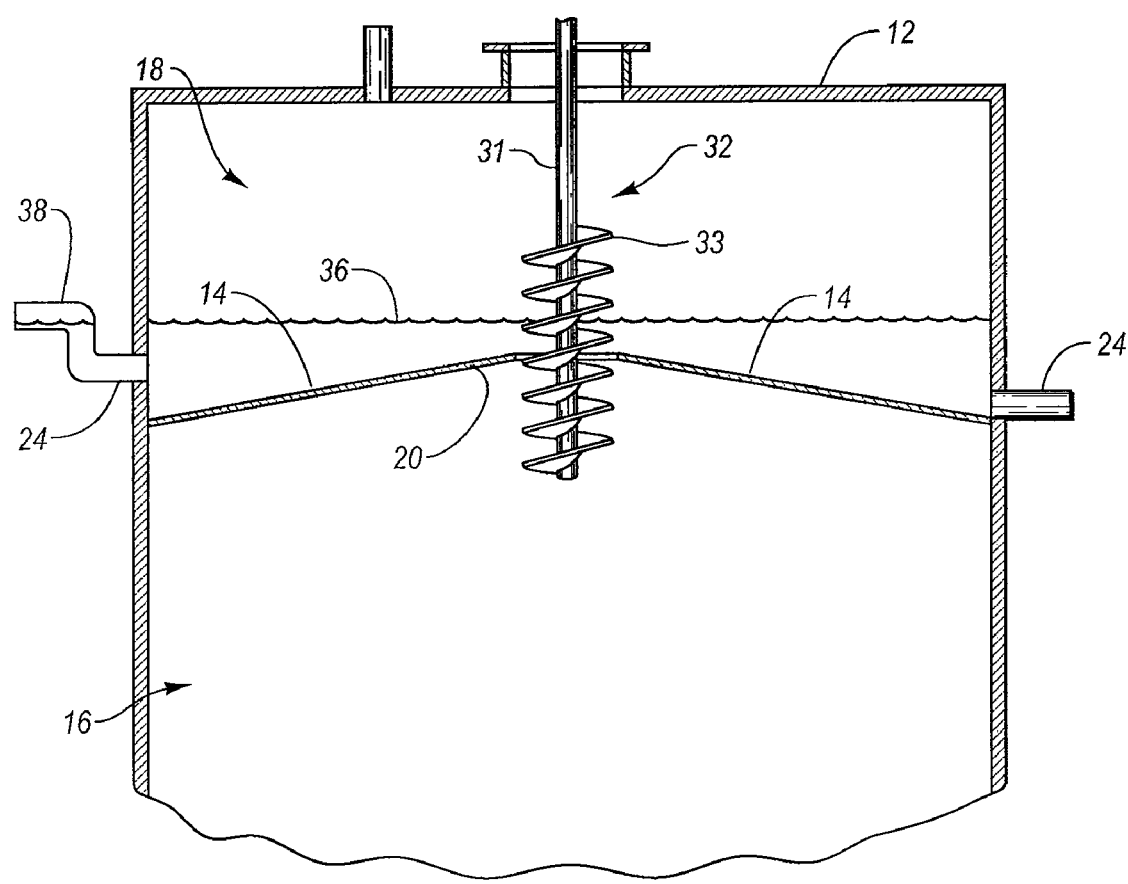
FIG. 2 is a cross-sectional view of a portion of the bioreactor of FIG. 1.

FIG. 2 shows a cross-section of a portion of bioreactor 10. The fluids within vessel 12 have a fluid level 36. Fluid level 36 is maintained by effluent outlet 24 and/or effluent line 38. Fluid level 36 is set below the top of vessel 12 such that a gas collection chamber is formed between the bioreactor fluids and the top of vessel 12.

Septum 14 is positioned within vessel 12 below fluid level 36. Septum 14 can be rigid or semi-rigid and can be made from any material compatible with the bioreactor fluids, including but not limited to plastics, metals, and the like. Septum 14 can be formed from a plurality of panels, or it can be a single, unitary piece of material. Septum 14 can be secured to the inside of the vessel 12 in any manner.

In one embodiment septum 14 slopes upwardly from the sidewalls of vessel 12 toward aperture 20. Sloping septum 14 can facilitate the removal of materials that settle out in upper chamber 18. A sloped septum can also be advantageous for ensuring that biogas in lower chamber 16 is directed to aperture 20. However, the present invention can also be carried out using a flat septum.

An auger 32 is positioned within aperture 20 of septum 14. Auger 32 can be any device that can be positioned within aperture 20 and can move solids in a desired direction between or within upper and lower chambers 16 and 18. In an exemplary embodiment, the auger includes a shaft with one or more flanges that are configured to move a material in a direction parallel to the shaft. Auger 32, shown in FIG. 2, includes a shaft 31 and a continuously spiraling flange 33.

In one embodiment, auger 32 creates a force that is opposite the flow of fluids in the bioreactor. For example, auger 32 can have a flange 33 such that when auger 32 is rotated clockwise, the auger creates a force that is opposite the flow of the bioreactor fluids. During optimal or "normal" operating conditions, auger 32 is rotated in the direction that counters the flow of the bioreactor fluids. This counter-flow force tends to settle out solids suspended in the effluent passing through aperture 20. If aperture 20 becomes clogged, the auger can be rotated in an opposite direction to remove solids to above the septum 14 where the solids can be more easily removed.

Auger 32 and septum 14 are provided to help form and maintain biomass 26. By retaining the bacteria within the lower chamber 16, septum 14 and auger 32 retain more bacteria, which are available for breaking down the organic material being fed into bioreactor 10. By utilizing the auger and septum, organic materials can be treated much faster and much more efficiently than organic waste being digested in other bioreactors. In addition, use of the septum and auger improves the clarity of effluent exiting the bioreactor.

Figure 3:
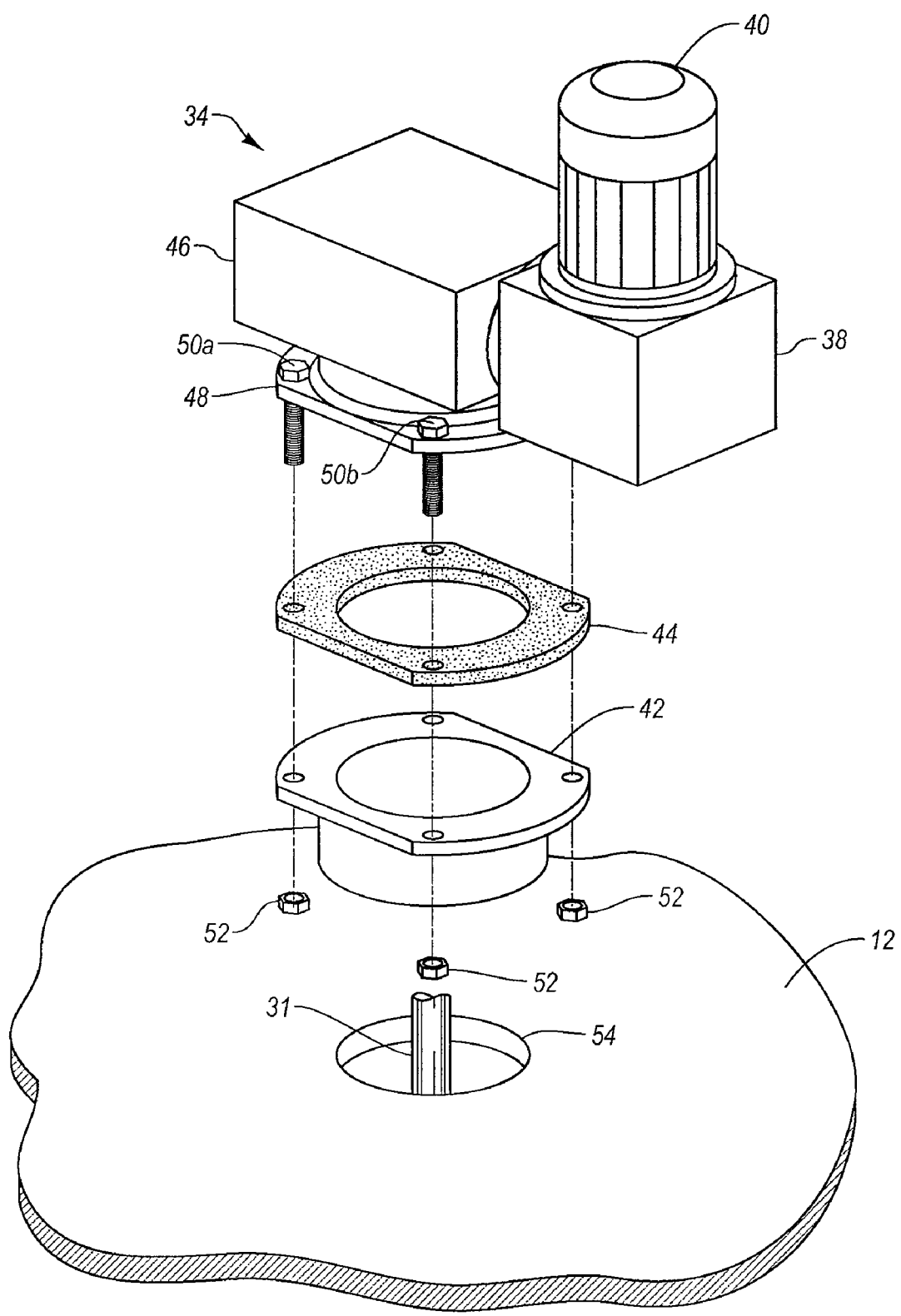
FIG. 3 is an exploded view of the auger and drive assembly of the bioreactor of FIG. 1.

FIG. 3 illustrates an example drive assembly 30 having an adjustment mechanism (or means) according to one embodiment of the present invention. Drive assembly 30 is positioned over an opening 54 in the top of vessel 12. Opening 54 allows shaft 31 of auger 32 to exit vessel 12 and couple with the drive assembly. Drive assembly 30 includes a gearbox 34, a second reduction gearbox 38, and a motor 40. Drive assembly 30 also includes a spacer bracket 42 and a compressible member 44.

Gearbox 34 is configured to be attached to spacer bracket 42. Gearbox 34 includes a drive housing 46 that includes a flange 48. Flange 48 has a plurality of holes that allow drive housing 46 to be attached to spacer bracket 42 using a plurality of bolts 50. Spacer bracket 42 includes a plurality of holes that align with the holes of flange 48 to receive bolts 50. Bolts 50 can be secured to flange 48 and spacer 42 using a plurality of nuts 52 attached in a known fashion. In this embodiment, other known fastening mechanisms can be used in place of bolts 50 and nuts 52 so long as the mechanism is adjustable.

Compressible member 44 is positioned between bracket 42 and flange 48. Compressible member 44, spacer bracket 42 and flange 48 are configured to create a seal around opening 54 in the top of vessel 12. To maintain a sealed gas chamber in the top of vessel 12, drive assembly 30 creates a seal around opening 54. In one embodiment, spacer bracket 42 is welded to vessel 12, and compressible member 44 maintains a seal between bracket 42 and drive housing 46 when drive housing 46 is attached thereto.

In one embodiment of the invention, drive housing 46 is part of a drive mechanism that rotates shaft 31. In one embodiment the drive mechanism is a gearbox 34 that includes a drive shaft and a plurality of gears within gearbox 34. The drive shaft extends from a wall of gearbox 34 and a bearing in the wall provides a fluid seal around the shaft 31. A lubricant within the gearbox 34 provides a gas seal over the fluid sealed bearing. Those skilled in the art are familiar with gearboxes, drive shafts and bearings that seal drive shafts. Using the gearbox 34 as a seal for the drive mechanism to the auger 32 is advantageous because it simplifies the number of pieces needed to form the gas seal and facilitates an auger 32 and drive assembly 30 that is one single unit that can be easily installed, removed, or repaired.

Figure 4A:
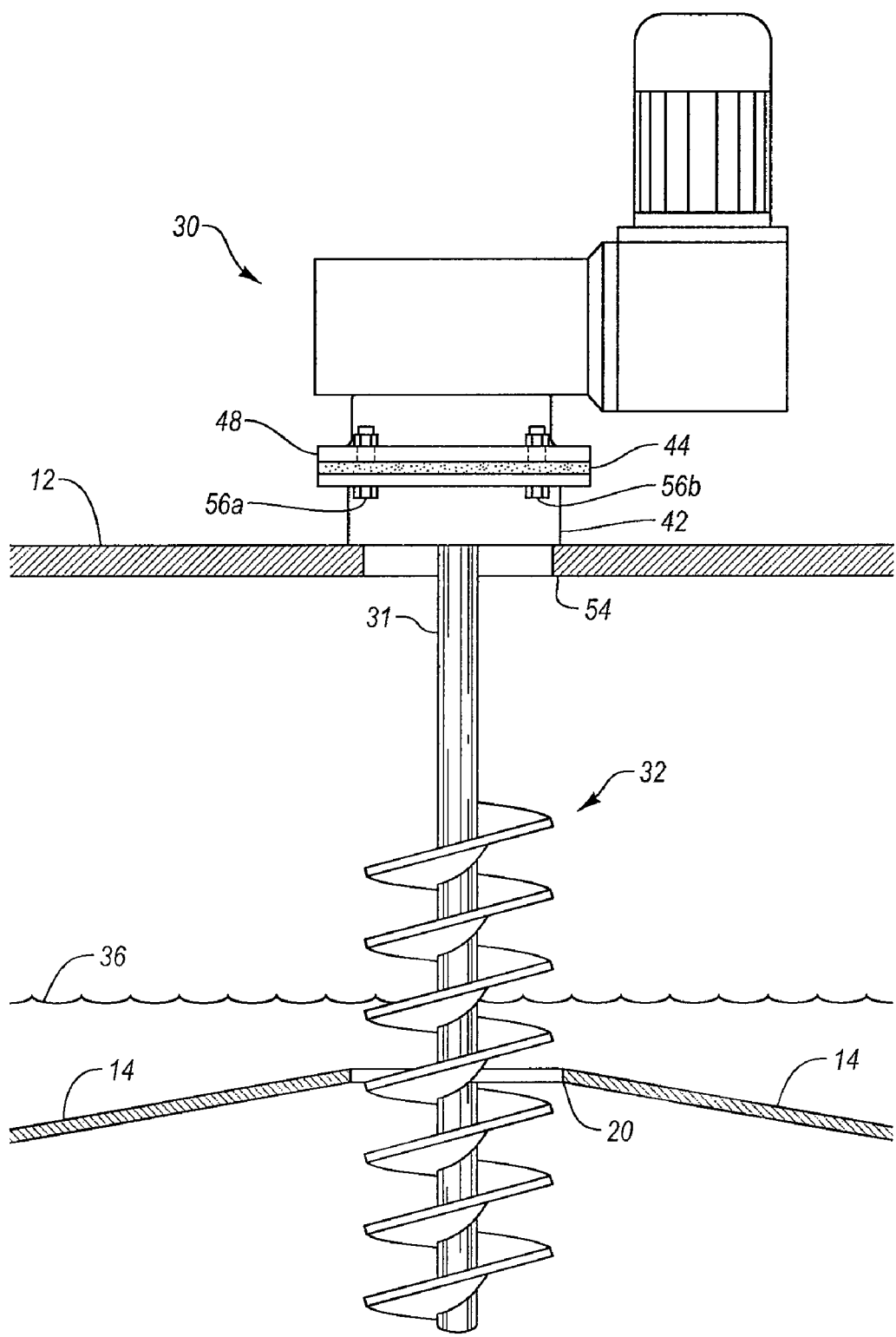
FIG. 4A is a cross-sectional side view of a portion of the bioreactor of FIG. 1 and a side view of the auger and drive assembly of the bioreactor of FIG. 1.
Figure 4B:
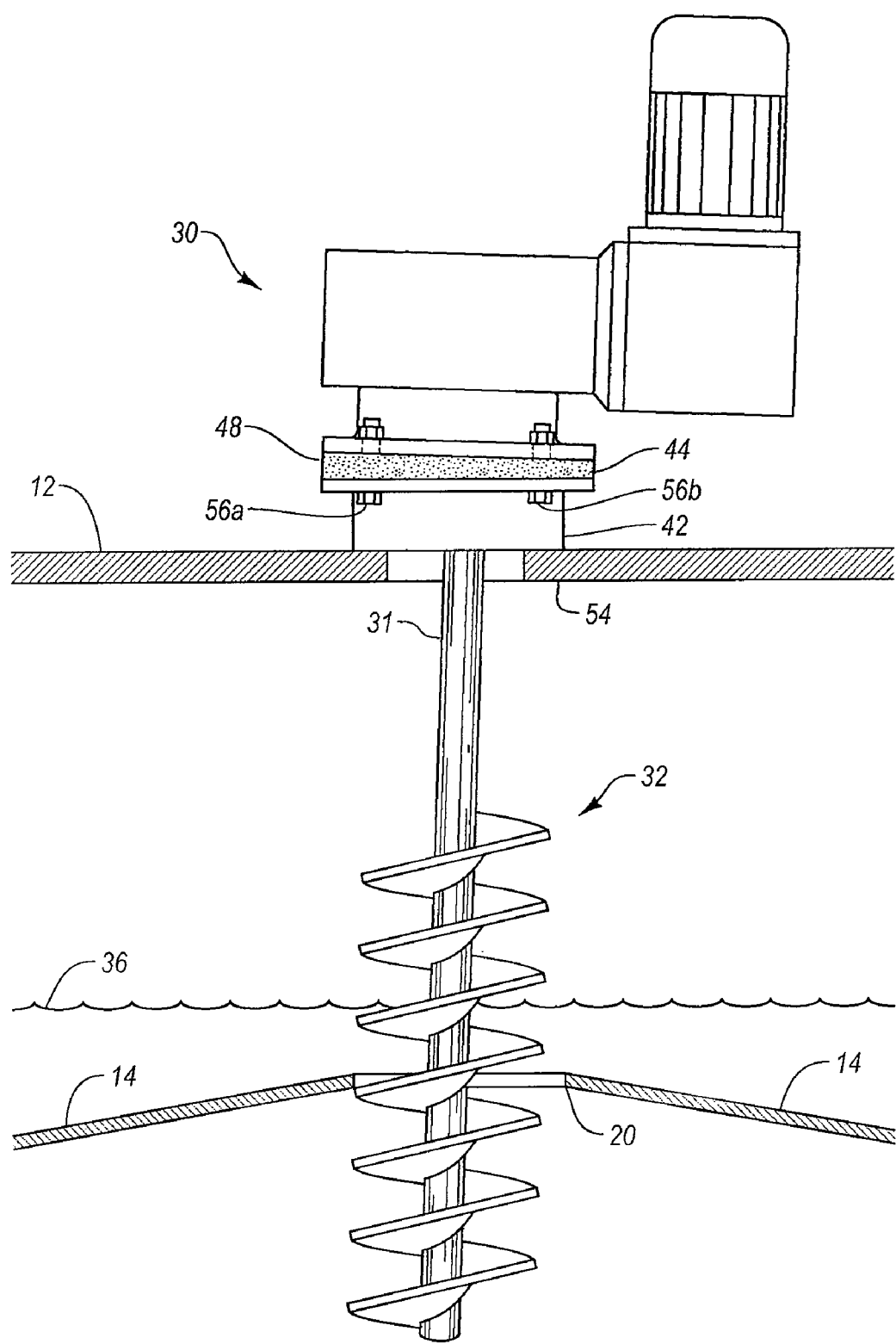
FIG. 4B is a side view illustrating the adjustment mechanism of FIG. 4A with a portion of an adjustment mechanism compressed.

FIGS. 4A and 4B show drive assembly 30 attached to vessel 12. Bolts 50 and nuts 52 are coupled to form fasteners 56a and 56b. Fasteners 56a and 56b in combination with compressible member 44 are an example of an auger adjustment mechanism (or means) according to one embodiment of the present invention. Fastener 56a and 56b can be selectively engaged to cause selective compression of compressible member 44, which provide means for laterally adjusting the auger 32 relative to the septum 14 (e.g., aperture 20 of septum 14).

For example, FIG. 4B shows fastener 56b more tightly threaded than fastener 56a thereby selectively compressing the portion of compressible member 44 near fastener 56b. The selective compression of a member 44 causes drive assembly 30 and auger 32 to tilt. When drive assembly 30 tilts, the position of auger 32 moves laterally with respect to septum 14. Selectively compressing member 44 allows auger 32 to be positioned within a desired location in aperture 20.

The amount of lateral adjustability depends on the thickness of the compressible member 44, the extent to which member 44 can be compressed and the distance between compressible member 44 and aperture 20. The amount that the drive assembly and auger pivot depends on the amount that the compressible member is selectively compressed. However, because the motion is a pivoting motion, the lateral movement of the auger relative to the septum depends on the distance that the septum is from the pivot point. Therefore, small changes in the compression of member 44 translate into a relatively large lateral movement of auger 32 relative to septum 14.

In an embodiment of the invention, the distance between compressible member 44 and aperture 20 of septum 14 is in a range from 0.5 meter to 2 meters, alternatively in a range from 1 meter to 1.5 meter. In one embodiment, the thickness of compressible member 44 is at least ⅛ inch, alternatively at least ¼ inch or at least ½ inch. Compressible member 44 can be made from any material that can be compressed while providing a seal. An example of a suitable material includes rubber. The compressible member is preferably elastically deformable such that releasing the compressive force results in an expansion. However, if desired, materials that plastically deform when compressed can also be used, with the caveat that once compressed they will not spontaneously return to a more expanded condition when the compressive force is released.

The present invention can be carried out using any number of adjustable fasteners (i.e., one or more fasteners). Providing at least three spaced apart fasteners has the advantage of allowing selective compression within a plane, which translates into selective movement of the auger in all directions relative to the plane of the septum.

Figure 5:
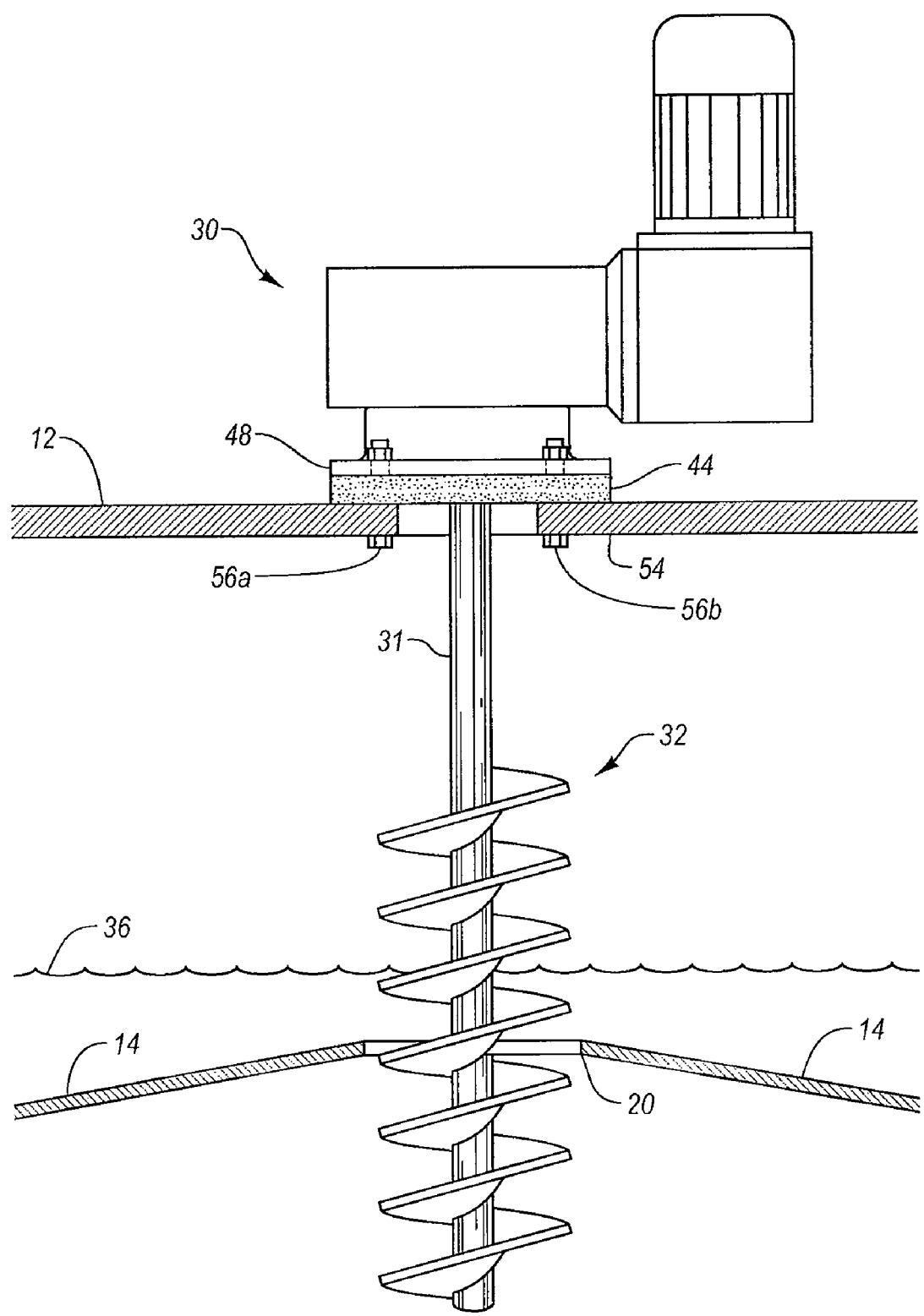
FIG. 5 is a cross-sectional side view of a portion of the bioreactor of FIG. 1 and a side view of an alternative drive assembly according to an alternative embodiment of the invention.

FIG. 5 shows an alternative embodiment of the invention where the spacer bracket 42 is removed and compressible member 44 and drive housing 48 are secured directly to vessel 12. In one embodiment, the bolts of fasteners 56a and 56b can be welded to vessel 12 to seal the holes through which fasteners 56a and 56b are placed. In this embodiment, the auger adjustment mechanism performs substantially similar to the auger adjustment mechanism described with reference to FIGS. 4A and 4B.

Figure 6A:
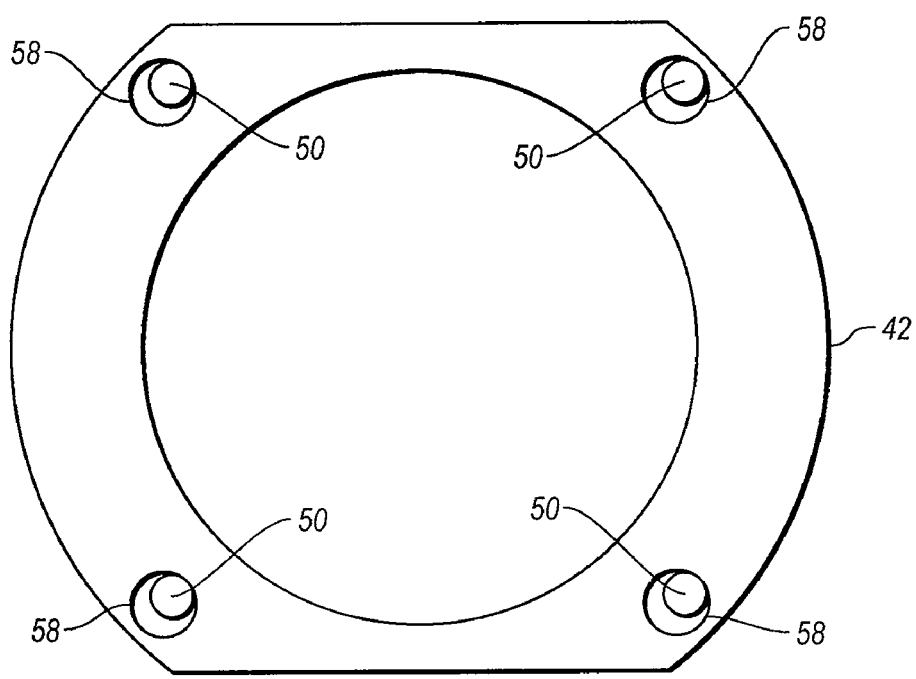
FIG. 6A is a top view of the spacer bracket of the bioreactor of FIG. 1 showing a bolting pattern having an adjustment mechanism according to an alternative embodiment of the present invention.
Figure 6B:
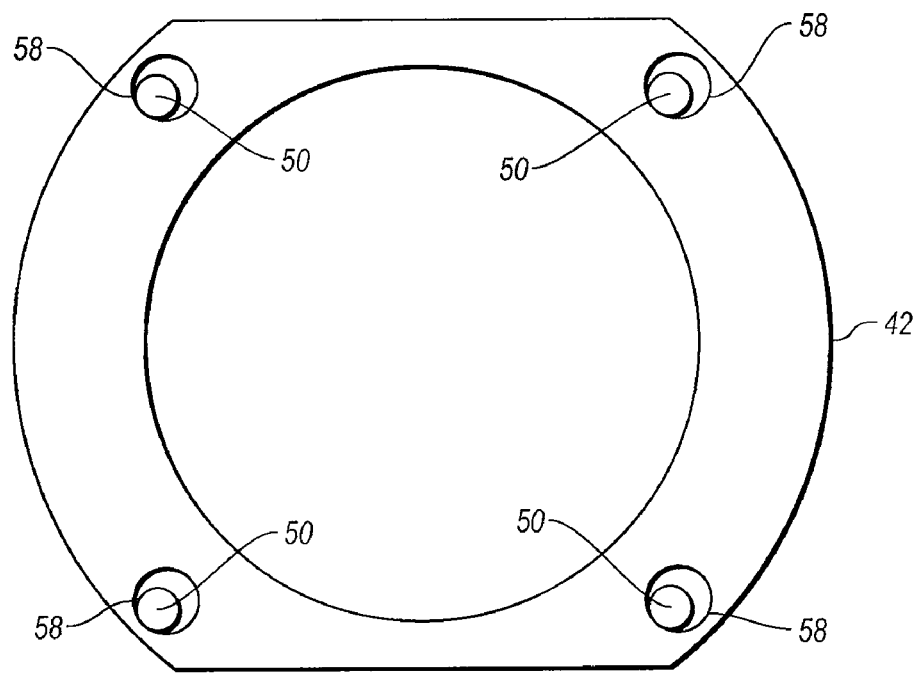
FIG. 6B is a top view of the spacer bracket of FIG. 6A showing an adjustment in the bolting pattern with respect to the spacer bracket.

In yet another alternative embodiment, the auger adjustment mechanism comprises a bolt and hole pattern that allows substantial lateral movement of a bolt within the mounting holes of flange 48 and/or spacer bracket 42. FIGS. 6A and 6B show a top view of a spacer bracket 42 with oversized mounting holes 58. Bolts 50, which extend through holes of drive housing 46 (FIG. 3) can be selectively moved within mounting holes 58. In FIG. 6A bolts 50 are in a first position and in FIG. 6B, bolts 50 are shifted laterally to a second position. The lateral adjustability of bolts 50 within mounting holes 58 allows drive housing 46 to be shifted laterally, which results in a lateral shift of auger 32 relative to septum 16 (FIG. 3).

Whether a mounting hole is oversized depends on the size of the bolt being placed in the mounting hole. In one embodiment, the diameter of the mounting hole is more than 10% larger than the diameter of the bolt, alternatively more than 25% larger, or more than 50% larger.

The auger adjustment mechanism provided by oversized mounting holes can be implemented independently or in combination with a compressible member.

While various embodiments of the present invention have been described as utilizing a bolt and nut as a fastener, those skilled in the art will recognize that there are other fasteners and fastening mechanisms that can be implemented to carry out the invention. In addition, those skilled in the art will recognize that the bolt and/or nut can be integrated into various parts of the drive assembly and/or vessel. For example, instead of a nut, the drive housing, mounting bracket, or vessel may have threads formed in a mounting hole. Similarly, a bolt may be integrated into the drive housing, mounting bracket, or vessel.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An upflow bioreactor comprising:
   a vessel having an inlet, an outlet, and a top opening, wherein the top opening is configured to receive an auger and drive assembly;
   a septum positioned within the vessel and defining a lower chamber and an upper chamber, the septum having an aperture that provides fluid communication between the lower chamber and the upper chamber; and
   an auger and drive assembly comprising a drive housing and an auger, wherein the drive housing is mounted over the top opening and forms a gas seal around the top opening and wherein the auger extends from the drive housing through the aperture in the septum, the drive assembly including an adjustment mechanism that allows mounting the drive assembly to be selectively adjusted relative to the vessel in order to cause lateral movement of the auger relative to the septum.

2. An upflow bioreactor as in claim 1, in which the adjustment mechanism permits lateral movement of the auger of at least 1 inch relative to the septum.

3. An upflow bioreactor as in claim 1, wherein the adjustment mechanism comprises (i) a compressible member positioned between the vessel and a drive housing of the drive assembly and (ii) one or more fasteners that can be selectively tightened so as to compress at least a portion of the compressible member.

4. An upflow bioreactor as in claim 3, in which the adjustment mechanism comprises at least three spaced apart fasteners that can be selectively and independently tightened to cause selective compression of the compressible member.

5. An upflow bioreactor as in claim 3, in which the compressible member has a thickness of at least about ⅛ inch.

6. An upflow bioreactor as in claim 3, in which the compressible member comprises rubber.

7. An upflow bioreactor as in claim 1, in which the adjustment mechanism comprises a plurality of oversized mounting holes configured to receive a plurality of fasteners attached to the drive assembly, respectively, wherein the diameter of each mounting hole is at least 10% greater than the diameter of a corresponding fastener.

8. An upflow bioreactor as in claim 1, in which the diameter of each mounting hole is at least 50% greater than the diameter of a corresponding fastener.

9. An upflow bioreactor as in claim 1, in which the drive assembly comprises a fluid.

10. An upflow bioreactor as in claim 1, in which the drive assembly comprises a gearbox.

11. An upflow bioreactor as in claim 1, further comprising a biomass within the lower chamber, the biomass comprising anaerobic bacteria.

12. An upflow bioreactor as in claim 1, wherein the upper chamber is sealed such that gas produced in the lower chamber can be collected in the upper chamber and introduced into a gas outlet.

13. An upflow bioreactor as in claim 1, in which the inlet is positioned in the lower chamber and the outlet is positioned in the upper chamber such that an upflow is created during operation of the bioreactor.

14. An upflow bioreactor comprising:
a vessel having an inlet, an outlet, and a top opening, wherein the top opening is configured to receive an auger and drive assembly;
a septum positioned within the vessel and defining a lower chamber and an upper chamber, the septum having an aperture that provides fluid communication between the lower chamber and the upper chamber; and
an auger and drive assembly comprising a drive housing and an auger, wherein the drive housing is mounted over the top opening and forms a gas seal around the top opening and wherein the auger extends from the drive housing through the aperture in the septum, the drive assembly including an adjustment mechanism comprising a compressible member and one or more fasteners configured to selectively compress a portion of the compressible member and wherein selectively compressing a portion of the compressible member causes a lateral movement of the auger relative to the septum.

15. A bioreactor as in claim 14, in which the drive housing is part of a gearbox, the gearbox comprising:
a drive shaft that is operably connected to the auger;
a bearing positioned in a wall of the gearbox and providing a fluid seal around the drive shaft; and
a lubricant in the gearbox.

16. A bioreactor as in claim 14, wherein a spacer bracket is positioned between the drive housing and the vessel.

17. A bioreactor as in claim 14, wherein the drive housing is bolted directly to a wall of the vessel.

18. An upflow bioreactor as in claim 14, in which the compressible member has a thickness of at least about ⅛ inch.

19. An upflow bioreactor as in claim 14, in which the compressible member has a thickness of at least about ¼ inch.

20. An upflow bioreactor as in claim 14, in which the compressible member has a thickness of at least about ½ inch.

21. An upflow bioreactor comprising:
a vessel having an inlet, an outlet, and a top opening, wherein the top opening is configured to receive an auger and drive assembly;
a septum positioned within the vessel and defining a lower chamber and an upper chamber, the septum having an aperture that provides fluid communication between the lower chamber and the upper chamber; and
an auger and drive assembly comprising a gearbox and an auger, wherein the gearbox comprises,
a drive shaft extending from a wall of the vessel and being operably connected to the auger;
a bearing positioned in the wall of the gearbox and providing a fluid seal around the drive shaft; and
a lubricant in the gearbox; and
wherein the gearbox is mounted on the vessel over the top opening such that the auger and gearbox assembly form a gas seal around the top opening of the vessel.

22. A bioreactor as in claim 21, wherein a spacer bracket is positioned between a housing of the gearbox and the vessel.

23. A bioreactor as in claim 21, further comprising an auger adjustment mechanism.

* * * * *

UNITED STATES PATENT AND TRADEMARK OFFICE
CERTIFICATE OF CORRECTION

| | | |
|---|---|---|
| PATENT NO. | : 7,290,669 B1 | Page 1 of 2 |
| APPLICATION NO. | : 11/553518 | |
| DATED | : November 6, 2007 | |
| INVENTOR(S) | : Hansen et al. | |

It is certified that error appears in the above-identified patent and that said Letters Patent is hereby corrected as shown below:

Title Page
Item (57), abstract, line 9, change "position" to --positioned--

Drawings
Sheet 5, replace Figure 4B with the figure depicted herein below, wherein reference "48" has been adjusted to correctly illustrate the "flange"

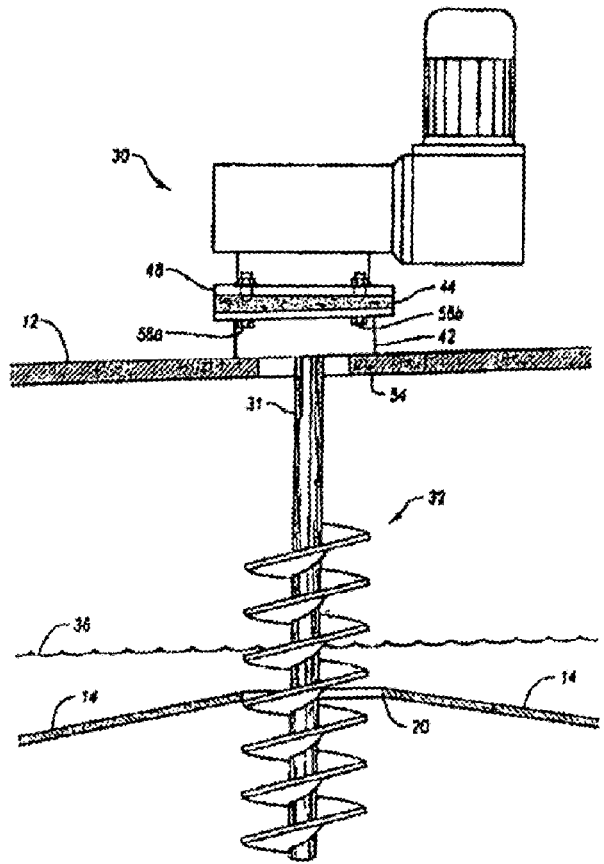

Fig. 4B

UNITED STATES PATENT AND TRADEMARK OFFICE
CERTIFICATE OF CORRECTION

PATENT NO. : 7,290,669 B1 Page 2 of 2
APPLICATION NO. : 11/553518
DATED : November 6, 2007
INVENTOR(S) : Hansen et al.

It is certified that error appears in the above-identified patent and that said Letters Patent is hereby corrected as shown below:

<u>Column 7</u>
Line 28, change "48" to --46--
Line 48, change "16" to --14--

Signed and Sealed this

Fifteenth Day of July, 2008

JON W. DUDAS
*Director of the United States Patent and Trademark Office*